United States Patent [19]

Wu et al.

[11] Patent Number: 5,846,729
[45] Date of Patent: Dec. 8, 1998

[54] ASSAYING NUCLEOTIDES IN SOLUTION USING A FLUORESCENT INTENSITY QUENCHING EFFECT

[75] Inventors: Yuan Min Wu; Eileen Xiao-Feng Nie, both of Thornhill, Canada

[73] Assignee: Lorne Park Research, Inc., Toronto, Canada

[21] Appl. No.: 886,280

[22] Filed: Jul. 1, 1997

Related U.S. Application Data

[63] Continuation-in-part of Ser. No. 807,901, Feb. 27, 1997.

[51] Int. Cl.$^6$ ........................................................ C12Q 1/68
[52] U.S. Cl. .............................. 435/6; 435/810; 436/501; 536/23.1; 536/24.1; 536/24.3; 536/24.31; 536/24.32; 536/24.33; 536/25.3; 935/77; 935/78
[58] Field of Search ........................ 435/6, 810; 436/501; 536/22.1, 23.1, 24.1, 24.3–24.33, 25.3; 935/77, 78

[56] References Cited

U.S. PATENT DOCUMENTS

| | | | |
|---|---|---|---|
| 4,220,450 | 9/1980 | Maggio | 23/230 B |
| 4,963,477 | 10/1990 | Tchen | 435/6 |
| 5,217,866 | 6/1993 | Summerton et al. | 435/6 |
| 5,332,659 | 7/1994 | Kidwell | 435/6 |
| 5,503,980 | 4/1996 | Cantor | 435/6 |
| 5,538,848 | 7/1996 | Livak et al. | 435/5 |
| 5,539,082 | 7/1996 | Nielsen et al. | 530/300 |
| 5,594,138 | 1/1997 | Dykstra et al. | 540/596 |
| 5,674,698 | 10/1997 | Zarling et al. | 435/7.92 |
| 5,747,247 | 5/1998 | Kowalczykowski et al. | 435/6 |

FOREIGN PATENT DOCUMENTS

| | | |
|---|---|---|
| 0 232 967 | 8/1987 | European Pat. Off. . |
| 92/18650 | 10/1992 | WIPO . |
| 93/24652 | 12/1993 | WIPO . |
| 94/25477 | 11/1994 | WIPO . |
| 97/12995 | 4/1997 | WIPO . |

OTHER PUBLICATIONS

"PNA Oligomers as Hybridization Probes", vol. 1, Issue 2 of Perseptive Biosystems Magazine, 1995.
C. Garisson et al., "Screening for genetic mutations," 380 Nature 207 (Mar. 21, 1996).
Perry–O'Keefe et al., "Peptide Nucleic Acid Pre–Gel Hybridization: An Alternative to Southern Hybridization," 93 Proc. Natl. Acad. Sci. USA 14670 (Dec. 1996).
Smulevitch et al., "Enhancement of Strand Inversion by Oligonucleotides Through Manipulation of Backbone Charge," 14 Nature Biotechnology 1700 (Dec. 1996) (disclosed in Landsdorp, Close Encounters of the PNA Kind, 14 Nature Biotechnology 1653 (Dec. 1996).
Lansdorp, "Close Encounters of the PNA Kind," 14 Nature Biotechnology 1653 (Dec. 1996).
Egholm et al., "PNA Hybridizes to Complementary Oligonucleotides Obeying the Watson–Crick Hydrogen–Bonding Rules," 365 Nature 566 (1993).
Tomac et al., "Ionic Effects on the Stability and Conformation of Peptide Nucleic Acid Complexes," 118 J.Am.Chem. Soc. 5544 (1996).
Coghlan, "One–step DNA test in a tube," New Scientist, p. 21 (Nov. 5, 1994).

(List continued on next page.)

*Primary Examiner*—Ardin H. Marschel
*Attorney, Agent, or Firm*—Caesar, Rivise, Bernstein, Cohen & Pokotilow, Ltd.

[57] ABSTRACT

The invention provides a method for rapidly, economically and efficiently sequencing and assaying nucleotides in a liquid medium using laser induced fluorescence of antisense probes, including PNA probes. Fluorescent intensity of the resulting medium is inversely proportional to the hybridization efficiency of the probes with respect to the target sequence. The method is particularly advantageous in not requiring separation of unhybridized probes and hybridization complexes prior to detection. The method can be used to identify accessible regions in folded nucleotide sequences, to determine the number of mismatched pairs in a hybridization complex, and to map genomes.

28 Claims, 10 Drawing Sheets

OTHER PUBLICATIONS

Heppell–Parton, "Gene Mapping by Fluorescence in Situ Hybridization," pp. 350–354, in *Molecular Biology and Biotechnology: A Comprehensive Desk Reference* (Myers, ed. 1995).

Rawls, "Optimistic About Antisense," 75(22) Chem. Eng. News 35, 39 (Jun. 2, 1997).

Matthews et al., "Analytical Strategies for the Use of DNA Probes," 169 Analytical Biochemistry 1 (1988).

Jensen et al., "Kinetics for Hybridization of Peptide Nucleic Acids (PNA) with DNA and RNA Studied with the BIAcore Technique," 36(16) Biochem. 5072 (Apr. 1997).

ASSAYING NUCLEOTIDES IN SOLUTION USING A FLUORESCENT INTENSITY QUENCHING EFFECT

CROSS-REFERENCE TO RELATED APPLICATION

This application is a continuation-in-part of our earlier U.S. application Ser. No. 08/807,901, filed Feb. 27, 1997 and entitled "ASSAYING NUCLEOTIDES IN SOLUTION USING PNA PROBES".

BACKGROUND OF THE INVENTION

1. Field of Invention

The invention relates to methods of sequencing or assaying nucleotides in solution, without the need for solid support or adjacent double stranded nucleotide construct, using a fluorescent intensity quenching effect exhibited by antisense probes, such as peptide nucleic acid (PNA) probes.

2. Description of Related Art

PNAs are polyamide analogs of DNA and RNA. See, e.g., U.S. Pat. No. 5,539,082 to Nielsen et al. Nielsen et al. discloses that PNAs mimic natural polynucleotides by binding complementary single stranded (ss) DNA and RNA strands. PNAs generally comprise ligands linked to a peptide backbone. Representative ligands include either the four main naturally occurring DNA bases (i.e., thymine, cytosine, adenine or guanine) or other naturally occurring nucleobases (e.g., inosine, uracil, 5-methylcytosine or thiouracil) or artificial bases (e.g., bromothymine, azaadenines or azaguanines, etc.) attached to a peptide backbone through a suitable linker.

Probes comprising PNA sequences have been employed to detect target nucleotide sequences. U.S. Pat. No. 5,503,980 to Cantor suggests employing PNA probes in a method of sequencing a nucleic acid by hybridizing the nucleic acid with a set of PNA probes containing random, but determinable, base sequences within the single stranded portion adjacent to a double stranded portion, wherein the single stranded portion of the set preferably comprises every possible combination of sequences over a predetermined range. Hybridization occurs by complementary recognition of the single stranded portion of a target with the single stranded portion of the probe and is thermodynamically favored by the presence of adjacent double strandedness of the probe.

However, although Cantor discloses that the nucleic acids can be PNAs, it does not disclose or suggest utilizing such probes in the absence of a solid support. Moreover, the present invention does not require the adjacent construct of DNA material being tested.

In addition to teaching the use of a solid support like Cantor, Perry-O'Keefe et al., "Peptide Nucleic Acid Pre-Gel Hybridization: An Alternative to Southern Hybridization," 93 Proc. Natl. Acad. Sci. USA 14670 (December 1996) also teaches atthat PNA does not generally bind well to double stranded DNA (dsDNA). See Perry-O'Keefe et al. at page 14673, footnote. Moreover, the homopyrimidine PNA constructs which have been found to bind dsDNA well would not be useful as probes. Applicants have discovered that the qualification which suggests that only homopyrimidine can bind with dsDNA by strand invasion is incorrect and arises from the hybridization conditions employed.

Smulevitch et al., "Enhancement of Strand Inversion by Oligonucleotides Through Manipulation of Backbone Charge," 14 Nature Biotechnology 1700 (December 1996) (disclosed in Landsdorp, "Close Encounters of the PNA Kind," 14 Nature Biotechnology 1653 (December 1996)) discloses using PNA primers to hybridize with dsDNA. However, Smulevitch et al. teaches the use of gels in detecting hybridization, and does not suggest the use of fluorescent markers.

Many types of sample analysis rely upon the fluorescent properties of a marker. Fluorescence occurs when a molecule excited by light of one wavelength returns to the unexcited (ground) state by emitting light of a longer wavelength. The exciting and emitted light, being of different wavelengths, can be separated from one another using optical filters, a camera or a CCD. Fluorescence has been used to visualize certain molecules (and hence structures) by light microscopy for many years, and is also used in other analytical techniques, such as flow cytometry. Further, the emission of fluorescence showing different colors can be detected by a human eye, a camera, a charge coupled device (CCD) or a photomultiplier.

For example, U.S. Pat. No. 5,594,138 to Dykstra et al. discloses a method of fluorescent detection of a nucleic acid. The method comprises contacting the nucleic acid with a fluorescent marker that is a bis-dicationic aryl furan compound and exposing the nucleic acid to light at a frequency inducing fluorescence of the fluorescent marker. The fluorescent marker may be conjugated to a nucleotide sequence as a probe for hybridization studies, or it may be conjugated to numerous reagents for in situ labeling studies. Hybridization occurs on a solid support.

U.S. Pat. No. 4,963,477 to Tchen discloses a probe of high sensitivity containing a modified nucleic acid, which can be recognized by specific antibodies.

Fluorescent In Situ Hybridization (FISH) is a technique comprising detecting fluorescent probe binding to human chromosomes by attaching DNA to a solid support, such as a glass slide. See, e.g., K. H. Andy Choo, Ed., "In Situ Hybridization Protocols," Chapters 2 and 4 (Humana Press, Totowa, N.J., 1994). Like all other conventional detection methods comprising hybridization with probes, this method relies on the solid support to keep the two complementary strands of DNA apart while the probe hybridizes with one of the strands. In addition, FISH requires a complicated buffer and temperature control protocol, with overnight incubation.

U.S. Pat. Nos. 5,538,848 to Livak et al. and 4,220,450 to Maggio disclose fluorescence-based detection of nucleotide sequences using oligonucleotide probes in solution; however, these patents require the use of a quenching agent in combination with a reporting agent, so as to distinguish between the signals generated by hybridized probes and unhybridized probes. Livak et al. also requires the use of enzymes in its disclosed method. Quenching agents and enzymes add complexity and expense to the methods.

U.S. Pat. No. 5,332,659 to Kidwell discloses a method for detecting nucleotide sequences in solution using probes comprising at least two fluorophore moieties. The fluorophores must be selected to electronically interact with each other when close enough to vary the wavelength dependence of their spectra. Unhybridized probes are much more flexible than probes hybridized to the target sequence, and consequently the two fluorophore moieties on each probe are more likely to be close to each other when the probe is unhybridized than when the probe is hybridized. Thus, a change in emission wavelength correlated with free probe can be monitored as an indication of the amount of free probe in the sample.

Until the present invention, however, it has not been possible to rapidly test for the presence of nucleotide sequences in solution using a method which does not destroy the sample, is less hazardous to laboratory personnel than radiation based assays, does not require the cost and delay of separating unhybridized probes from hybridization complexes, does not require the provision of quenching agents, does not require the provision of enzymes, does not require the provision of multiple interactive reporting moieties on each probe and is readily automated. Time and cost efficient detection of mutant genetic sequences has been the rate limiting step in correlating mutant genotypes with altered phenotypes. Although conventional DNA sequencing methods have been considered to be the most accurate means of identifying mutations, these methods have been relatively slow and labor intensive, and are not particularly well-suited to rapidly screening large numbers of samples of genomic DNA for purposes including medical diagnosis, genomic sequencing and mapping.

All references cited herein are incorporated herein by reference in their entireties.

SUMMARY OF THE INVENTION

The present invention provides methods for detecting nucleic acid sequences and/or determining sequence information, including genomic sequence information, from nucleic acids using probes comprising DNA, RNA, DNA analogs and/or RNA analogs (hereinafter "antisense probes").

The invention provides a method for detecting at least one single stranded or double stranded nucleotide sequence in a liquid medium. The method comprises: (1) adding to the liquid medium at least one antisense probe having at least one marker to form at least one hybridization complex with at least one nucleotide sequence in the medium; and (2) detecting the at least one nucleotide sequence by detecting at least one signal that is inversely proportional to an amount of the at least one hybridization complex in the liquid medium and proportional to an amount of the at least one probe unhybridized in the liquid medium. The method can be conducted without separating unhybridized probes from the at least one hybridization complex prior to signal detecting, without providing a signal quenching agent on the at least one probe or on the at least one nucleotide sequence, and without the use of enzymes. The method can be employed to map genomes by screening a genomic library with a plurality of probes.

BRIEF DESCRIPTION OF THE DRAWINGS

The invention will be described in conjunction with the following drawings in which like reference numerals designate like elements and wherein.

DETAILED DESCRIPTION OF PREFERRED EMBODIMENTS

Figure 1A:
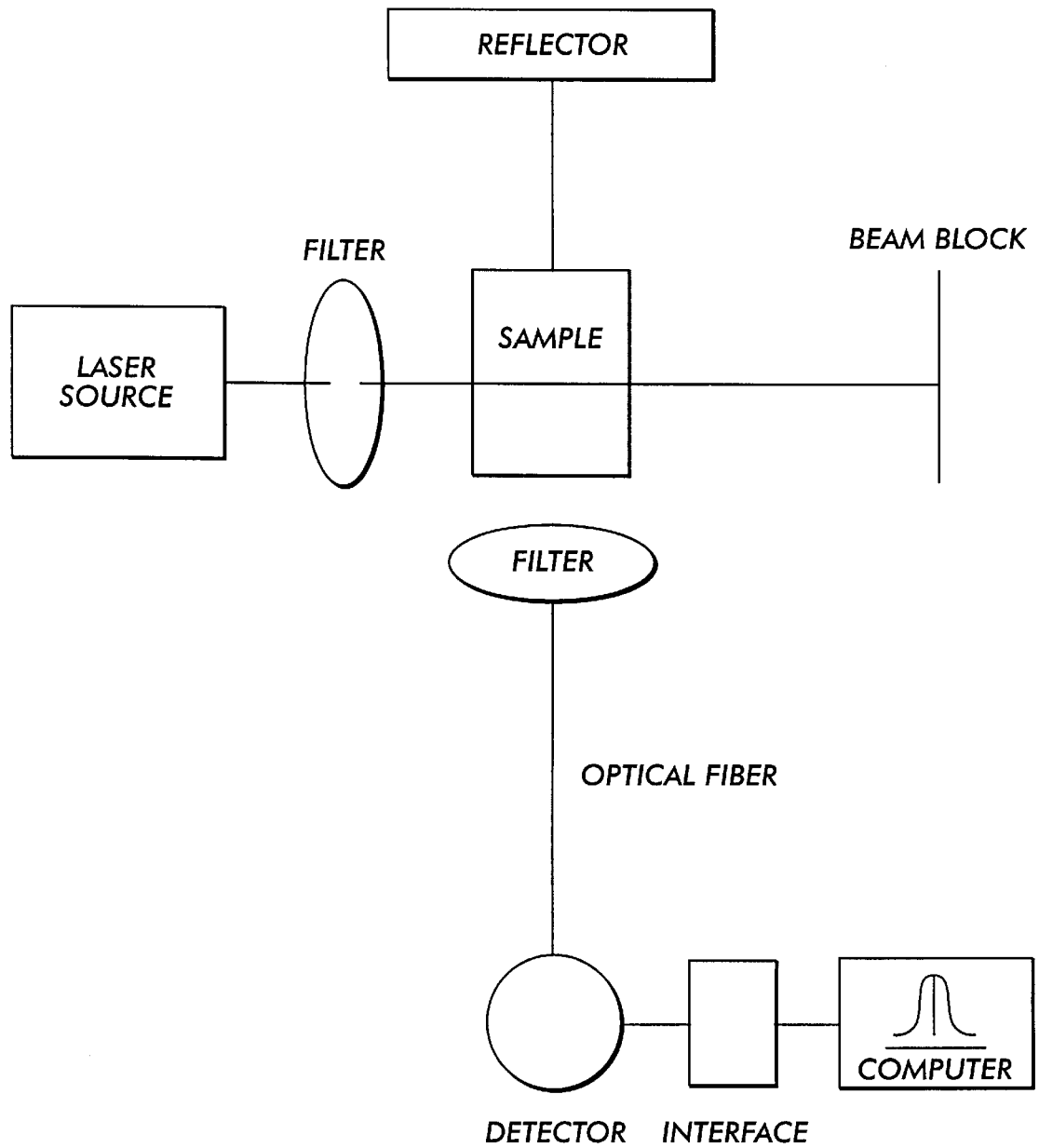
FIG. 1A is a schematic depiction of an embodiment of an apparatus according to the invention.

The invention utilizes antisense probes to detect and/or characterize nucleotide sequences in a sample. The expression "antisense probes" as used herein includes any probe capable of specifically binding to a nucleotide sequence having a base sequence complementary to the base sequence of the probe. The antisense probes of the invention can be complementary to either strand of dsDNA, for example. PNA probes are most preferred, and are the focus of much this specification, but the invention is not limited thereto.

PNA probes are able to recognize dsDNA by hybridizing one strand, thereby presumably binding with the other strand to generate a PNA-DNA complex. Such recognition can take place to dsDNA target sequences 20 or more base pairs long. Probe sequences having any length from 8 to 20 bases are preferred since this is the range within which the smallest unique DNA sequences of prokaryotes and eukaryotes are found. Probes of 12 to 18 bases are particularly preferred since this is the length of the smallest unique sequences in the human genome. However, a plurality of shorter probes can be used to detect a nucleotide sequence having a plurality of non-unique target sequences therein, which combine to uniquely identify the nucleotide sequence.

At least the PNA probes of the invention are able to form triplex complexes with dsDNA and duplex complexes with RNA or ssDNA. The PNA probes of the invention are also able to form triplex complexes wherein a first PNA probe binds with RNA or ssDNA and a second ssDNA strand binds with the resulting duplex complex. See, e.g., Egholm et al., "PNA Hybridizes to Complementary Oligonucleotides Obeying the Watson-Crick Hydrogen-Bonding Rules," 365 Nature 566 (1993), and Tomac et al., "Ionic Effects on the Stability and Conformation of Peptide Nucleic Acid Complexes," 118 J.Am.Chem.Soc. 5544 (1996).

In the PNA probes according to the invention, the bases attached to the polyamide backbone are primarily naturally occurring nucleobases attached at the position required by probe manufacture. Alternatively, the bases may be non-naturally occurring nucleobases (nucleobase analogs), other base-binding moieties, aromatic moieties, (C1–C4) alkanoyls, hydroxyls or even hydrogens. It will be understood that the term nucleobase includes nucleobases bearing removable protecting groups. Furthermore, at least one base on the polyamide skeleton can be replaced with, or substituted with, a DNA intercalator, a reporter ligand such as, for example, a fluorophore, radio label, spin label, hapten, or a protein-recognizing ligand such as biotin. Preferred detectable labels include a radioisotope, a stable isotope, an enzyme, a fluorescent chemical, a luminescent chemical, a chromatic chemical, a metal, an electric charge, or a spatial structure.

In particularly preferred embodiments, the probe comprises an antisense sequence covalently bonded to a fluorescent marker, which fluoresces when irradiated with a laser. Preferred fluorescent markers include biotin, rhodamine and fluorescein.

The intensity of the fluorescence is proportional to the amount of free probe in solution and inversely proportional to the amount of hybridized probe in solution. That is, there is a quenching effect associated with hybridization of the probe and target sequence. The quenching effect varies with the marker selected. This effect enables the method of the invention to detect hybridization without employing a quenching agent on the probe (to quench unhybridized probe signal) or on the target sequence (to quench hybridized probe signal), as required by, e.g., Livak et al. and Maggio, supra.

Unlike Kidwell, supra, the instant invention does not require a plurality of electronically interacting fluorophores on each probe, because the fluorescent intensity quenching effect detected by the instant invention is not the same as the emission wavelength shift detected in Kidwell, which is caused by intramolecular excimer formation between adjacent fluorophores. The quenching effect of the instant invention is apparent with only one fluorophore per probe (although a plurality of fluorophores per probe are contemplated for certain embodiments).

In certain embodiments, the fluorescent marker is provided at the 5' terminal of the probe with a short linker to minimize interaction with the probe. However, the position of the marker within the probe does not appear to be particularly significant.

In order to distinguish a mutant nucleotide sequence from a reference nucleotide sequence, wherein the two sequences differ by as little as a single base, it is preferred to design the probe so that the mutant portion of the mutant nucleotide corresponds to the center of the probe. This design results in a higher hybridization yield and a more stable hybrid than when the mutant portion of the nucleotide corresponds to a terminus of the probe, since the bonding mismatch between probe and nucleotide is located centrally within the probe.

Probes are added to a liquid medium suspected of containing at least one nucleotide sequence, and/or a mutant version of the at least one sequence. The liquid medium can be any conventional medium known to be suitable for preserving nucleotides. See, e.g., Sambrook et al., "Molecular Cloning: A Lab Manual," 2d (1989). For example, the liquid medium can comprise nucleotides, water, buffers and surfactants.

The nucleotides in the liquid medium can be obtained from clinical samples by any conventional method, including an automated method. Examples of such methods are summarized in, e.g., Sambrook et al., Vol. 2, pp. 9.16–9.19 and 7.6 to 7.7. An example of an automated nucleic acid purifying apparatus is the BioRobot 9600 manufactured by Quiagen (Chatsworth, Calif., USA).

For example, a variety of diseases are known to be linked with the presence of mutant DNA in an individual's genome. If the sequences of the wild type DNA and the mutant DNA are known, it is possible to isolate these nucleotide sequences from clinical samples using conventional technology. PCR is the preferred method of amplifying nucleotides from clinical samples. PCR is conducted using a primer which is capable of amplifying the wild type DNA and the mutant DNA.

The nucleotide sequences are added to the liquid medium in a known concentration, since the concentration can affect the magnitude of the signal (e.g., fluorescent intensity) generated in subsequent steps in the inventive method. The nucleotide concentration can be determined by, e.g., measuring the UV absorption at 260 nm.

The isolated nucleotides are added to the liquid medium and denatured prior to being detected. Preferably, the denaturation is conducted at about 90° C. to about 100° C. from about 30 seconds to about 5 hours in the presence of PNA probe.

Preferably, probes are added to the liquid medium in a concentration 0.05 to 100 times the concentration of the nucleotide sequence to be detected.

Hybridization between complementary bases occurs under a wide variety of conditions having variations in temperature, salt concentration, electrostatic strength, and buffer composition. Examples of these conditions and methods for applying them are known in the art. See, e.g., Perry-O'Keefe et al., Egholm et al., Tomac et al., Sambrook et al., Vol. 2 pp. 9.47–9.55 and the Pre-Gel Hybridization Technique taught in Vol. 4, No. 3 of PerSeptive Biosystems Magazine.

It is preferred that hybridization complexes be formed at a temperature of about 4° C. to about 75° C. for about 2 minutes to about 24 hours. It is particularly preferred to conduct denaturing for no more than 60 minutes in the presence of PNA probe, after which the temperature is passively cooled to room temperature without quenching.

It is possible to facilitate hybridization in solution by using certain reagents. Preferred examples of these reagents include single stranded binding proteins such as Rec A protein, T4 gene 32 protein, *E. coli* single stranded binding protein, major or minor nucleic acid groove binding proteins, divalent ions, polyvalent ions, and intercalating substances such as ethidium bromide, actinomycin D, psoralen, and angelicin.

The preferred markers for use in the invention are fluorophores. As will be appreciated by the skilled artisan, the wavelength preferably selected to induce fluorescence of the fluorescent marker is known in the art as the "excitation maximum," i.e., that wavelength which is absorbed by a molecule and excites that molecule to a higher electronic state. When the marker molecule passes from the higher to a lower electronic state, the molecule emits a type of visible radiation, i.e., fluorescence, at a wavelength referred to as the "emission maximum." It is at least this fluorescence that is detected in the present invention. The detectable signal emitted by the compound can be detected using techniques known in the art, for example by observation with the human eye, using electronic means for detecting a generated wavelength (e.g., cameras and CCDs), and the like. Advantageously, the wavelength of fluorescence is sufficiently removed from that of the exciting light to allow good separation of the two wavelengths by optical filters.

The excitation wavelength is selected (by routine experimentation and/or conventional knowledge) to correspond to this excitation maximum for the marker being used, and is preferably 200 to 1000 nm. For example, when the marker is fluoroscein, the preferred wavelength of excitation is about 488 nm. Fluorescent dyes are preferably selected to have an emission wavelength of 200 to 1000 nm.

In preferred embodiments, an argon ion laser is used to irradiate the marker with light having a wavelength in a range of 400 to 520 nm, and fluorescent emission is detected in a range of 500 to 750 nm.

An apparatus for performing the inventive method can comprise a liquid medium container for containing the liquid medium; a laser for irradiating the nucleotide; a CCD fluorescence detector and/or photomultiplier for detecting fluorescence induced by the laser; a data analysis device for analyzing data generated by the fluorescence detector; and an output device which reports the data analysis generated by the data analysis device. See, e.g., FIG. 1A, which shows a schematic diagram of a fluorescence detection system suitable for use with the method of the invention.

Unlike certain prior art methods, no separation of the hybridization complexes from the uncomplexed probes is necessary in the present method. In certain prior art methods, unhybridized probes and hybridized probes must be separated to enhance the signal to noise ratio (i.e., the ratio of the hybridization complex signal to the unhybridized probe signal or noise), enabling detection of hybridization. In the present method, the change in the overall signal is monitored without performing the additional burdensome step of separating the hybridized and unhybridized probes. The inventors have discovered that nucleotide sequence information can be determined by monitoring a change in the overall signal intensity, which is a function of hybridization and hybridization efficiency.

In particular, the inventors have discovered a signal quenching effect related to probe-nucleotide hybridization, wherein the intensity of laser induced fluorescence of an unbound probe exceeds that of the same probe bound to a nucleotide sequence. Therefore, a solution lacking any target sequences for probes therein will fluoresce more intensely than an otherwise identical solution containing target sequences and thus probe-nucleotide hybridization complexes.

Moreover, the intensity of laser induced fluorescence of hybridized probes is inversely proportional to the hybridization efficiency of the probes for their target sequences. Therefore, a solution containing imperfectly complementary target sequences for probes therein will fluoresce more intensely than an otherwise identical solution containing perfectly complementary target sequences. A solution containing target sequences mismatching n bases of the probes therein will fluoresce more intensely than an otherwise identical solution containing target sequences mismatching less than n bases of the probes therein. Thus, a three mismatch solution fluoresces more intensely than a two mismatch solution, which fluoresces more intensely than a one mismatch solution, which fluoresces more intensely than a zero mismatch (completely complementary) solution.

The quenching effect can be used to obtain nucleotide sequence information in a variety of ways.

In embodiments, a predetermined amount of at least one PNA probe can be added to a predetermined volume of solution containing a predetermined amount of at least one nucleotide sequence to be detected. After subjecting the sample to hybridizing conditions, the sample's laser induced fluorescent intensity can be measured. Sequence information regarding the at least one nucleotide sequence in the sample can be determined by comparing the intensity with the intensity of at least one known sample against which the apparatus and the method are calibrated. Thus, a mutant form of the target sequence has been detected if, for example, (a) a sample containing DNA and PNA probes hybridizable to a sequence of wild type DNA, fluoresces significantly more intensely than (b) a standard sample containing a probe perfectly complementary to the same sequence of the wild type DNA.

Similarly, a mutant form of the target sequence is detected if the sample does not fluoresce significantly less intensely than a standard sample containing a mutant form of the target sequence.

A significant difference in intensity is defined for present purposes as a difference not attributable to mere experimental variation. In the cases studied thus far, the intensity of a perfectly matched PNA probe and sequence has been at least about 40% lower than the intensity (at the same wavelength) of an imperfectly matched PNA probe and the same sequence. This value will vary along with the hybridization efficiency of a given case. However, those of ordinary skill in the art will readily appreciate that the actual value for any case being analyzed can be obtained empirically without undue experimentation.

The quenching effect appears to be most pronounced for DNA/RNA analog probes having uncharged backbones, such as PNA and methylene methyl amino oligonucleotides. The specification largely focuses on the most preferred embodiment of the invention—assaying methods using PNA probes—but the invention also encompasses the use of other antisense probes (DNA, DNA analog, RNA and/or RNA analog probes).

Another embodiment of the invention comprises dividing a sample into equal portions and treating each portion as a separate sample as discussed above, except that a different probe is added to each portion. The intensities of the portions are compared to determine, inter alia, which probe is most complementary, and thus which target sequence is in the original sample. This embodiment of the method is advantageous in that the system does not need to be calibrated against a known sample.

Although solid supports and gels are not required to practice this invention, such supports can be used in embodiments of the invention for purposes other than separating hybridization complexes from unhybridized probes. For example, two similar types of probes differing by one base can be fixed to opposing internal surfaces of a container in which a sample is added. After subjecting the sample to hybridization conditions and fluorescence inducing radiation, the fluorescent intensity emanating from the opposing surfaces of the container can be compared to determine whether the sample contains a nucleotide sequence perfectly complementary to either or both types of probes fixed to the surface.

A plurality of probes can be employed simultaneously to achieve a variety of effects. Several probes targeted for different segments of a single nucleotide sequence can be employed to enhance the reliability of the detection method. Similarly, one probe can target one strand of dsDNA, while another probe can target the complementary strand of dsDNA.

A preferred method of detecting whether DNA is mutant type or the corresponding wild type comprises the simultaneous use of (a) a first type of probe targeted to a sequence that occurs in both the wild type and mutant type DNA but is otherwise unique, and (b) a second type of probe targeted to a sequence unique to the mutant type DNA, wherein the first and second types of probe have different markers that produce distinguishable signals. Thus, detection of the first probe signal indicates that the test was run properly (i.e., the first probe functions as a positive control) and detection of the second probe signal indicates that the mutant type DNA is present. For example, one probe can have a fluorescein marker exhibiting a fluorescent emission intensity peak at 525 nm while the other probe can have a rhodamine marker exhibiting a fluorescent emission intensity peak at 580 nm.

The speed, accuracy and efficiency with which the invention is able to yield sequence data, coupled with the ability of laser induced fluorescence of probes to localize sequence portions within a longer sequence, make the invention an alternative to the FISH method for mapping genomes (compare, e.g., Heppell-Parton, "Gene Mapping by Fluorescence in Situ Hybridization," p. 350–54, in *Molecular Biology and Biotechnology: A Comprehensive Desk Reference* (Myers, ed. 1995)).

The invention provides an efficient method for analyzing nucleotide conformation, which is particularly useful for designing antisense drugs. Antisense drugs typically target mRNA for hybridization with an antisense sequence, so as to prevent translation of the mRNA into undesirable proteins. Unfortunately, the in situ folding of mRNA prevents some sequence portions along its length from being accessible to antisense sequences. Until now, drug designers have located accessible sequences by a method in which a series of antisense nucleotides complementary to different portions of the target mRNA are combined with the mRNA, and the best binding antisense nucleotide, presumably corresponding to the most accessible portion of the mRNA, is identified through slow and laborious tissue culture experiments, which can take at least about 45 days. See, e.g., Rawls, "Optimistic About Antisense," 75(22) Chem. Eng. News 35, 39 (Jun. 2, 1997). The accessible portions of mRNA can be identified using the instant invention without tissue culture experiments, since laser induced fluorescent intensity is inversely proportional to hybridization efficiency. The sequence emitting the lowest intensity has the highest hybridization efficiency with the target mRNA, and is presumably complementary to a segment that is not obstructed by in situ folding of mRNA.

The probes can be marked antisense drugs and/or can be analogs thereof. For example, it might be advantageous to design phosphorothioate oligonucleotide antisense sequences by performing laser induced fluorescent studies with such sequences marked with a fluorophore or with PNA probes similarly marked.

Moreover, the invention enables the length and other features of the antisense drugs to be readily fine tuned to optimize hybridization efficiency.

In contrast to prior art nucleotide sequence detection methods, the present invention makes it possible to limit the total volume of the liquid medium (i.e., the sample to be analyzed) in certain embodiments to about 5 microliters. Typically, the total volume is about 5 microliters to about 2000 microliters.

When testing for dsDNA using PNA, if a result is obtained for which there remains doubt, a further test may be immediately performed on the sample by adding the complementary PNA probe to test the complementary strand of DNA. Alternatively, the PNA test can be done with both the PNA and complementary PNA probes hybridized to each of the denatured DNA strands in the first instance and at the same time.

For forensic applications, samples can be tested, stored and then retested because PNA is expelled from hybridization over a couple of days, and DNA recombines over time and does not degrade by this procedure. Accordingly, a sample frozen after testing can be subsequently retested in the same tube a number of times.

Clinical samples can be tested using at least 2000 times less chemicals or genomic material (5 microliters vs. 10 milliliters) than is typical in conventional methods. Therefore, even using 10 or 20 times the concentration of probe conventionally used, the tests still only consume ⅕th to ¹/₁₀th the amount of probe, while obtaining a very decisive result.

The invention will be illustrated in more detail with reference to the following Examples, but it should be understood that the present invention is not deemed to be limited thereto.

EXAMPLES

The DNA used in the Examples was amplified by PCR and purified using the QIAquick PCR Purification Kit (QIAGEN Inc., Chatsworth, Calif., USA). PCR was conducted using a GeneAmp PCR system 2400 from Perkin Elmer, with a hot start at 95° C. for 5 minutes. After adding Taq enzyme, 35 cycles were carried out as follows:
Denaturing: 94° C. for 30 secs.
Annealing: 45° C. for 45 secs. (45° C. is 5° C. lower than the primer Tm)
Extension: 72° C. for 30 secs. (1 kb/min.)×35.

PCR was conducted using a mixture comprising in 100 μl volume 10×reaction buffer (10 μl), 20 mM of MgCl₂ (10 μl), 10 mM of dNTP mixture (2), 25 pmol/μl of primer 1 (1 μl), 25 pmol/μl of primer 2 (1 μl), 10 ng to 100 mg/μl of DNA template (1 μl), dd H₂O (74 μl) and Taq polymerase (1 μl) (5 unit/μl).

The concentration of DNA in each sample was measured with a UV spectrometer at 260 nm. Three related fragments of DNA were used in the Examples.

SEQ ID NO:1 was a 150 base pair fragment of genomic DNA amplified and purified from wild type p53 DNA.

SEQ ID NO:2 was a 150 base pair fragment identical to the wild type fragment (SEQ ID NO:1) except for one base mutation at amino acid position 344 (bases 100–102) at which the wild type sequence CTG was changed to CAG.

SEQ ID NO:3 was a 150 base pair fragment identical to the wild type fragment (SEQ ID NO:1) except for one base mutation at amino acid position 344 (bases 100–102) at which the wild type sequence CTG was changed to CGG.

The PNA probes used in the Examples were synthesized by PerSeptive Biosystems, Inc. (Framingham, Mass., USA).

Probe No. 1 was a 12-mer PNA probe designed to be completely complementary to a 12 nucleotide segment of the 150 bp p53 wild type fragment (SEQ ID NO:1). The probe had the following structure:

5' H-Flu-O-CAT TCA GCT CTC Lys-CONH₂.

Probe No. 2 was a 12-mer PNA probe designed to be completely complementary to a 12 nucleotide segment of SEQ ID NO:2 and one a one base mismatch with SEQ ID NO:1. The probe had the following structure:

5' H-Flu-O-CAT TCT GCT CTC Lys-CONH₂.

Probe No. 3 was a 12-mer PNA probe designed to be complementary to a 12 nucleotide segment of the 150 bp p53 wild type fragment (SEQ ID NO:1). The probe had the following structure:

5' H-Rho-O-CAT TCA GCT CTC Lys-CONH₂.

Prior to testing, the apparatus was calibrated against a known sample.

PNA probes in the examples were obtained from master solutions. Each 0.04 pmol/μl master solution was prepared by mixing 50 μl of a 1 pmol/μl solution of the PNA probe in TFA (trifluoroacetic acid) and 1200 μl 0.5×TBE buffer to provide a PNA concentration of 0.04 pmol/μl. Each 0.05 pmol/μl master solution was prepared by mixing 40 μl of a 1 pmol/μl solution of the PNA probe in TFA (trifluoroacetic acid) and 760 μl 0.5×TBE buffer to provide a PNA concentration of 0.05 pmol/μl. Each 0.10 pmol/μl master solution was prepared by mixing 80 μl of a 1 pmol/μl solution of the PNA probe in TFA (trifluoroacetic acid) and 720 μl 0.5×TBE buffer to provide a PNA concentration of 0.10 pmol/μl. Each mixture was heated to 50° C., maintained at that temperature for 10 minutes and then cooled to room temperature over 20 minutes.

Fluorescence was induced and detected using the system schematically depicted in FIG. 1A. An argon ion laser (Ion Laser Technology, Salt Lake City, Utah, USA) was used along with an S2000 spectrometer (Ocean Optics, Inc., Dunedin, Fla., USA). The wavelength of the laser beam produced by the laser was 488 nm.

Example 1A 5 pmol of DNA (SEQ ID NO:1) was added into 125 μl of Probe No. 1 master solution (0.04 pmol PNA/μl) to provide a test solution comprising 5 pmol of SEQ ID NO:1, 5 pmol of Probe No. 1 and 120 μl 0.5×TBE buffer. The sample was heated at 95° C. for 10 minutes and hybridized at 25° C. for 30 minutes. After hybridization, the solution was immediately placed into a cuvette, irradiated with a laser beam and monitored for fluorescent emission.

Example 1B

Example 1A was repeated with SEQ ID NO:2 substituted for SEQ ID NO:1.

Figure 1B:
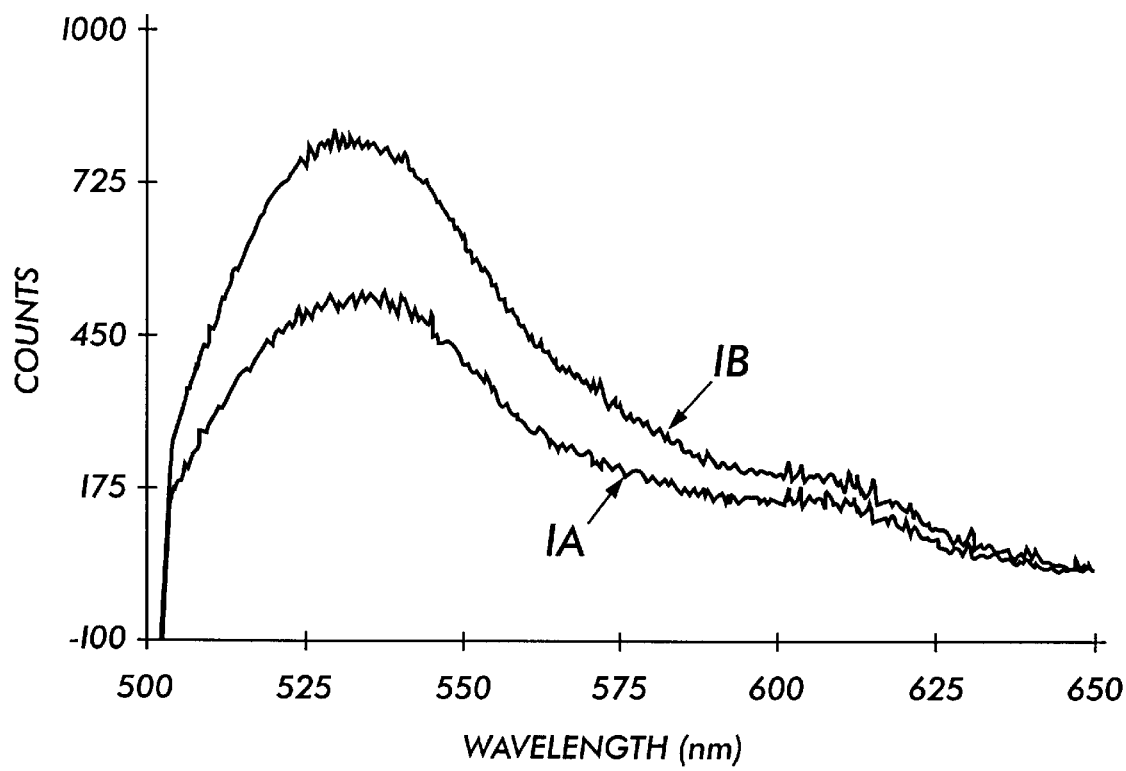
FIGS. 1B, 1C, 2, 3, and 4 are fluorescent spectra.

FIG. 1B shows the fluorescence spectra obtained in Examples 1A and 1B. The maximum fluorescent intensity occurred at about 525 nm, since the marker was fluorescein. The maximum intensity of the Example 1A solution, containing DNA hybridized to completely complementary PNA probes, was about 40% lower than the maximum intensity of the Example 1B solution, containing DNA hybridized to incompletely complementary PNA probes.

Example 1C

After the samples in Examples 1A and 1B had been subjected to laser induced fluorescence and detection, the hybridization complexes in each were separated from the unhybridized probes in each by spinning at 700 rpm for 2 minutes in G50 spin columns. Unhybridized probes were retained on the columns, while the hybridization complexes filtered through the columns and were collected in a cuvette for further laser induced fluorescence detection.

Figure 1C:
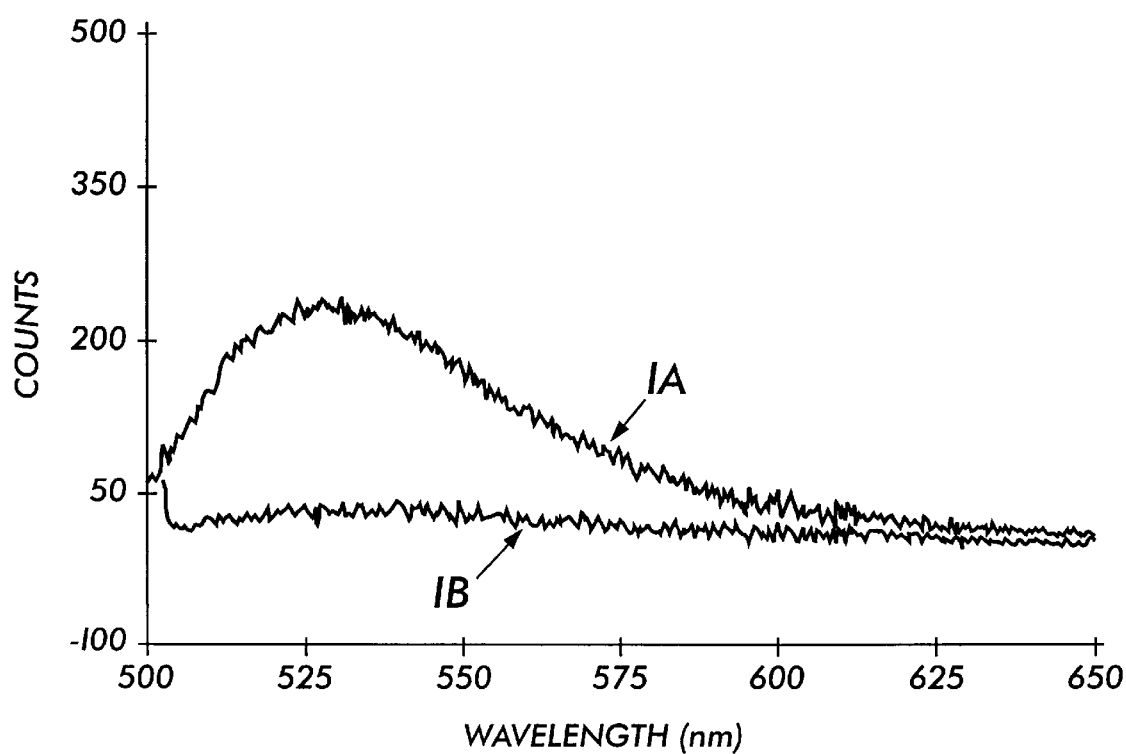

FIG. 1C shows the resulting fluorescence spectra. The trend is the opposite of that shown in FIG. 1B. That is, the perfectly matched PNA-DNA sample of Example 1A fluoresces more intensely than the imperfectly matched PNA-DNA sample of Example 1B. This is evidence that the hybridization yield in Example 1A is much higher than that in Example 1B.

Example 2A 4 pmol of SEQ ID NO:1 was added into 80 μl of Probe No. 1 master solution (0.05 pmol PNA/μl) to provide a test solution comprising 4 pmol of SEQ ID NO:1, 4 pmol of Probe No. 1 and 76 μl 0.5×TBE buffer. The sample was heated at 95° C. for 10 minutes and hybridized at 25° C. for 30 minutes. After hybridization, the solution was immediately placed into a cuvette, irradiated with a laser beam and monitored for fluorescent emission.

Example 2B

Example 2A was repeated with 3 pmol of SEQ ID NO:1 and 1 pmol of SEQ ID NO:2 substituted for 4 pmol of SEQ ID NO:1.

Example 2C

Example 2A was repeated with 2 pmol of SEQ ID NO:1 and 2 pmol of SEQ ID NO:2 substituted for 4 pmol of SEQ ID NO:1.

Example 2D

Example 2A was repeated with 1 pmol of SEQ ID NO:1 and 3 pmol of SEQ ID NO:2 substituted for 4 pmol of SEQ ID NO:1.

Example 2E

Example 2A was repeated with 4 pmol of SEQ ID NO:2 substituted for 4 pmol of SEQ ID NO:1.

Figure 2:
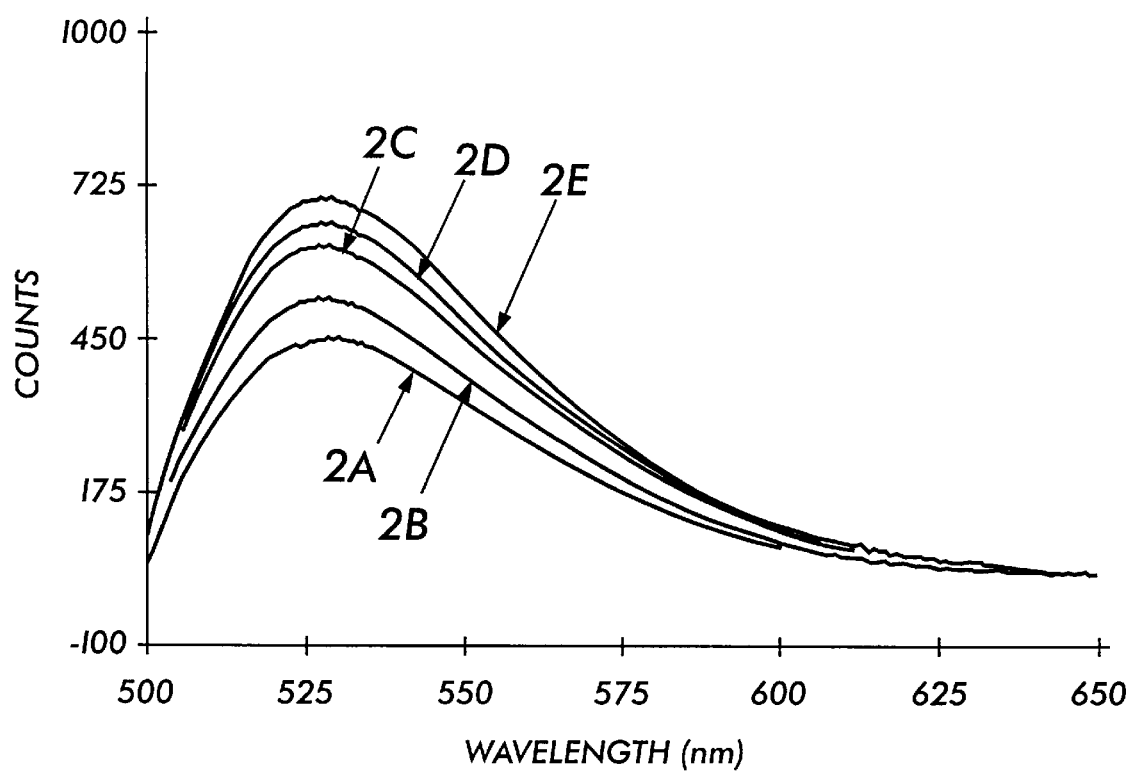

FIG. 2 shows the fluorescence spectra of Examples 2A–2E. Example 2A, having the highest percentage of perfect complements, yielded the lowest intensity, while Example 2E, having the lowest percentage of perfect complements, yielded the highest intensity. The fluorescent intensities decrease with increasing concentration of PNA-DNA hybridization complexes.

Example 3A 8 pmol of DNA (SEQ ID NO:1) was added into 80 μl of Probe No. 2 master solution (0.10 pmol PNA/μl) to provide a test solution comprising 8 pmol of SEQ ID NO:1, 8 pmol of Probe No. 2 and 72 μl 0.5×TBE buffer. The sample was heated at 95° C. for 10 minutes and hybridized at 25° C. for 30 minutes. After hybridization, the solution was immediately placed into a cuvette, irradiated with a laser beam and monitored for fluorescent emission.

Example 3B

Example 3A was repeated with SEQ ID NO:2 substituted for SEQ ID NO:1.

Example 3C

Example 3A was repeated with SEQ ID NO:3 substituted for SEQ ID NO:1.

Figure 3:
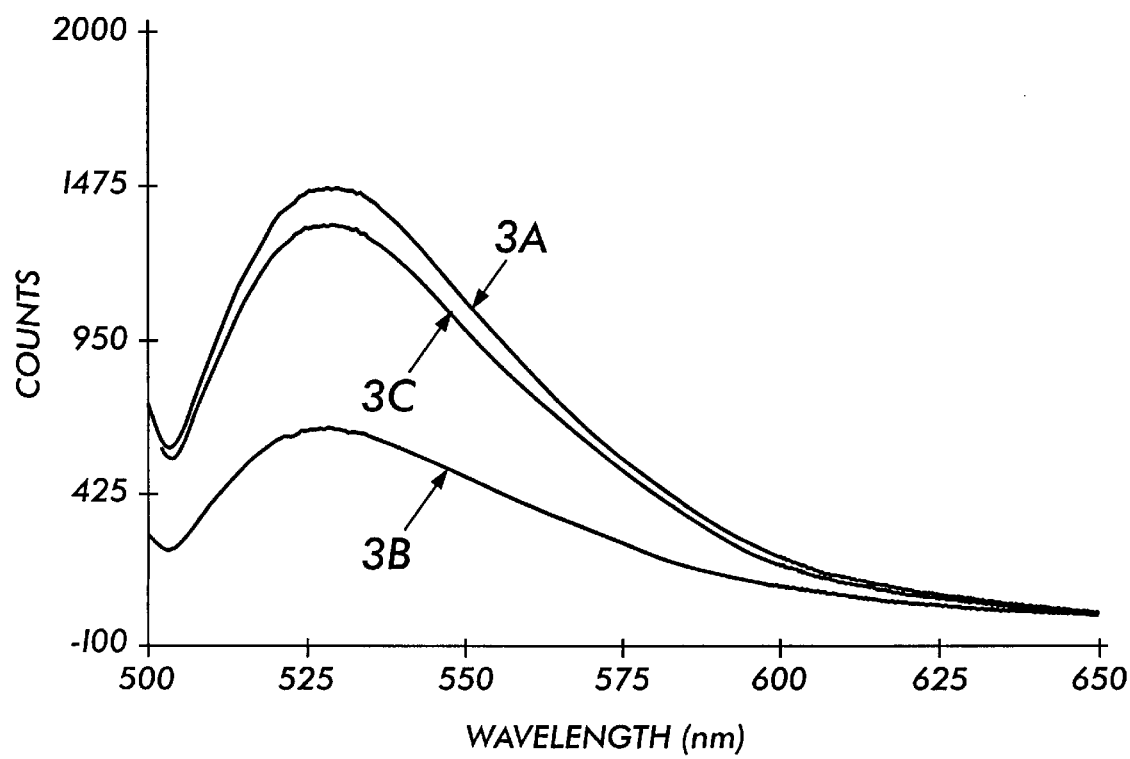

FIG. 3 shows the fluorescence spectra of Examples 3A–3C. The intensity of Example 3B, in which a completely complementary PNA probe and target sequence were combined, was significantly lower than the intensities of Examples 3A and 3C, in which incompletely complementary probes and targets were combined. The difference in intensities between Examples 3A and 3C is attributable to the type of mismatch between the respective probes and target sequences. Example 3C had an unfavorable G-T mismatch, while Example 3A had an even less favorable T-T mismatch, and thus Example 3A had the lowest hybridization efficiency and the highest intensity.

Example 4A 4 pmol of SEQ ID NO:1 was added into 80 μl of Probe No. 3 master solution (0.10 pmol PNA/μl) to provide a test solution comprising 4 pmol of SEQ ID NO:1, 8 pmol of Probe No. 3 and 72 μl 0.5×TBE buffer. The sample was heated at 95° C. for 10 minutes and hybridized at 25° C. for 30 minutes. After hybridization, the solution was immediately placed into a cuvette, irradiated with a laser beam and monitored for fluorescent emission.

Example 4B

Example 4A was repeated with SEQ ID NO:2 substituted for SEQ ID NO:1.

Figure 4:
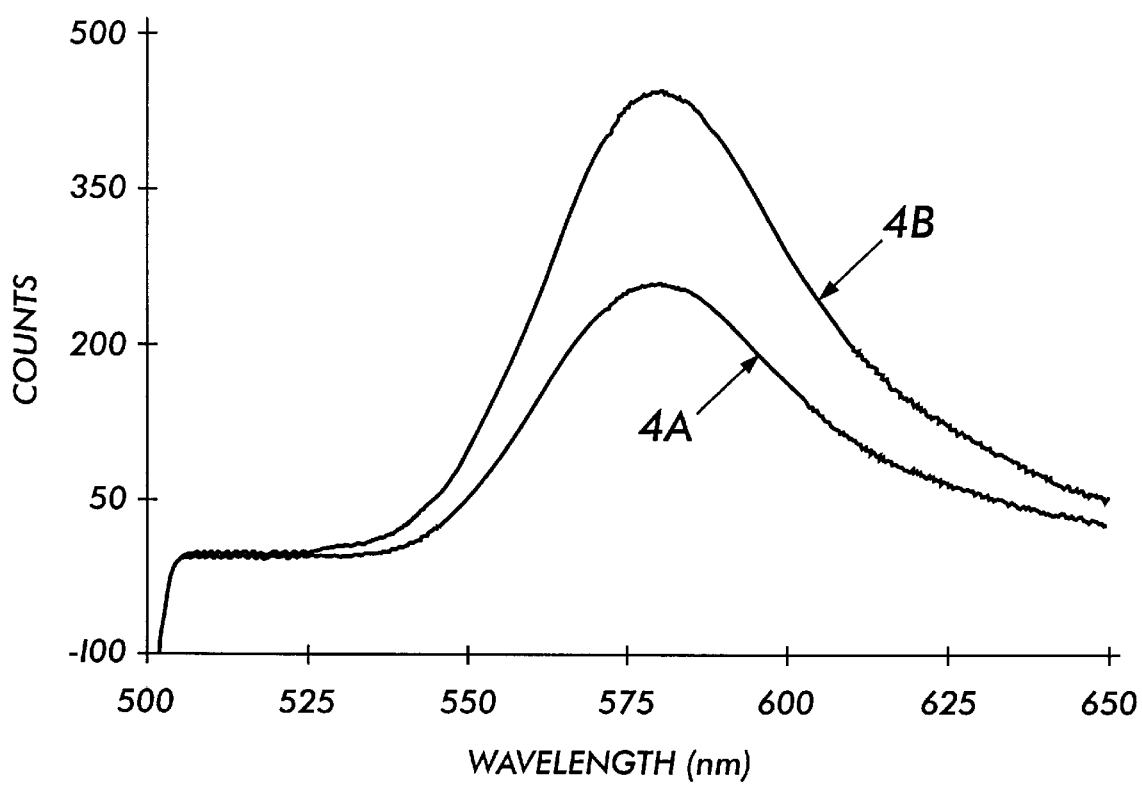

FIG. 4 shows the fluorescence spectra obtained in Examples 4A and 4B. The maximum fluorescent intensity occurred at about 580 nm, since the marker was rhodamine. The maximum intensity of the Example 4A solution, containing DNA hybridized to completely complementary PNA probes, was about 40% lower than the maximum intensity of the Example 4B solution, containing DNA hybridized to incompletely complementary PNA probes.

Example 5A

Figure 5:
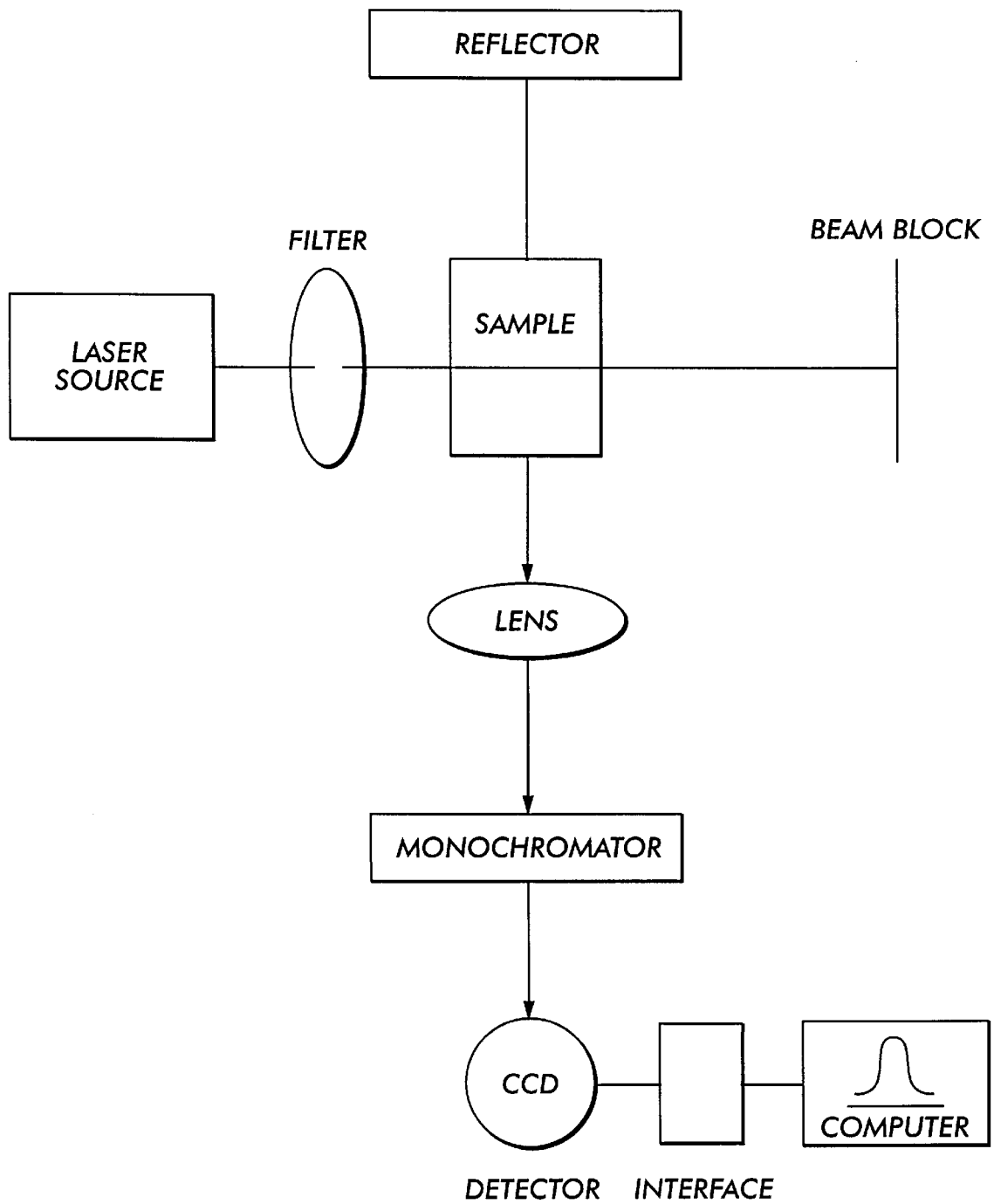
FIG. 5 is a schematic depiction of an embodiment of an apparatus according to the invention.

FIG. 5 is a schematic diagram of the fluorescent detection system used in this example, including an argon ion laser (Ion Laser Technology) as a light source and a CCD array (Princeton Instruments, Inc., Trenton, N.J., USA) as a detector.

4 pmol of SEQ ID NO:1 was added into 80 μl of Probe No. 1 master solution (0.05 pmol PNA/μl) to provide a test solution comprising 4 pmol of SEQ ID NO:1, 4 pmol of Probe No. 1 and 76 μl 0.5×TBE buffer. The sample was heated at 95° C. for 10 minutes and hybridized at 25° C. for 30 minutes. After hybridization, the solution was immediately placed into a cuvette, irradiated with a laser beam and monitored for fluorescent emission.

Example 5B

Example 5A was repeated with SEQ ID NO:3, which is a one base mismatch with Probe No. 1, substituted for SEQ ID NO:1.

Example 5C

Example 5A was repeated with SEQ ID NO:4, which is a two base mismatch with Probe No. 1, substituted for SEQ ID NO:1.

Example 5D

Example 5A was repeated with SEQ ID NO:5, which is a three base mismatch with Probe No. 1, substituted for SEQ ID NO:1.

Example 5E

Example 5A was repeated with SEQ ID NO:6, which lacks a target sequence for Probe No. 1, substituted for SEQ ID NO:1.

Figure 6:
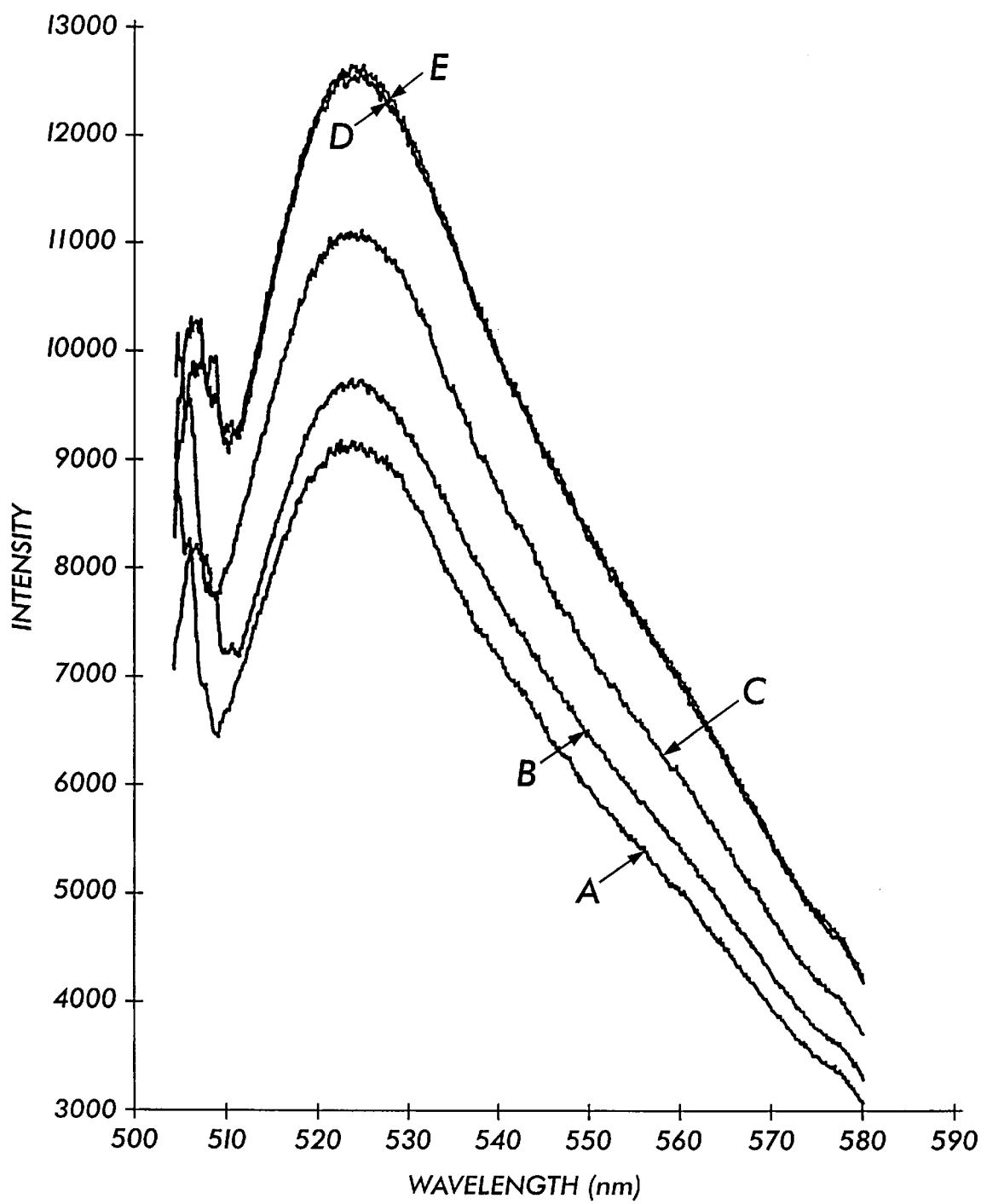
FIGS. 6, 7A, 7B, 8A and 8B are fluorescent spectra.

FIG. 6 shows the spectra obtained in Examples 5A–5E. The non-target sequence solution (5E) fluoresced more intensely than the three mismatch solution (5D), which fluoresced more intensely than the two mismatch solution (5C), which fluoresced more intensely than the one mismatch solution (5B), which fluoresced more intensely than the zero mismatch (completely complementary) solution (5A).

Example 6A 4 pmol of SEQ ID NO:1 was added into 80 µl of Probe No. 4 (5' Fluo-CAT TCA GCT CTC 3') master solution (0.10 pmol DNA/µl) to provide a test solution comprising 4 pmol of SEQ ID NO:1, 8 pmol of Probe No. 4 and 72 µl 0.5×TBE buffer. Probe No. 4 was a DNA probe designed to be completely complementary to a 12 nucleotide segment of SEQ ID NO:1. The sample was heated at 95° C. for 10 minutes and hybridized at 25° C. for 30 minutes. After hybridization, the solution was immediately placed into a cuvette, irradiated with a laser beam and monitored for fluorescent emission using the system schematically depicted in FIG. 5 and described in Example 5A.

Example 6B

Example 6A was repeated with SEQ ID NO:2 substituted for SEQ ID NO:1.

Figure 7A:
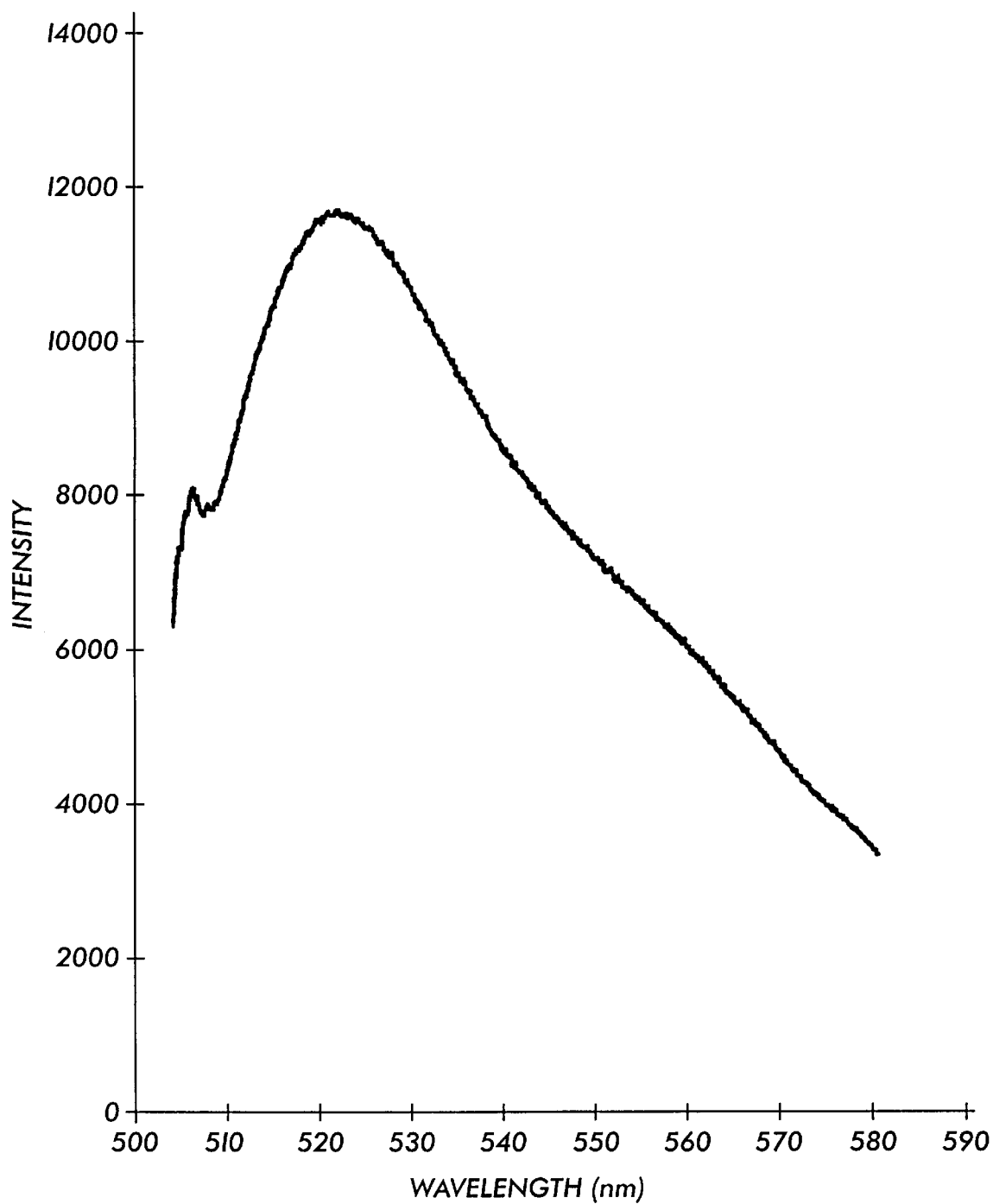
Figure 7B:
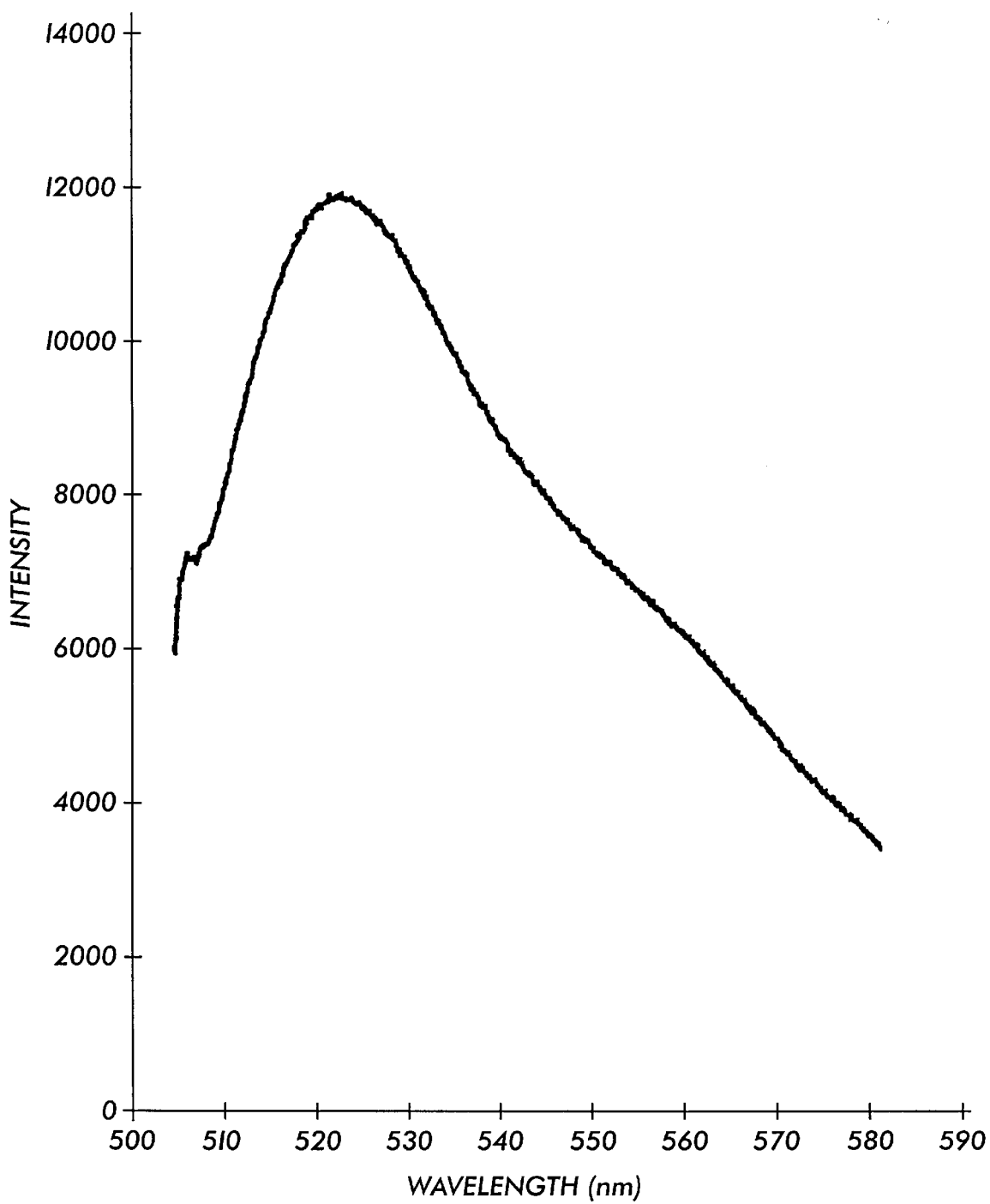

FIGS. 7A and 7B show the spectra obtained from Examples 6A and 6B, respectively. The fluorescent intensity of Example 6A (completely complementary) was slightly lower than that of Example 6B (one base pair mismatch).

Example 6C

After the samples in Examples 6A and 6B had been subjected to laser induced fluorescence and detection, any hybridization complexes in each were separated from the unhybridized probes in each by spinning at 700 rpm for 2 minutes in G50 spin columns. Unhybridized probes were retained on the columns, while any hybridization complexes would have filtered through the columns and been collected in a cuvette for further laser induced fluorescence detection.

Figure 8A:
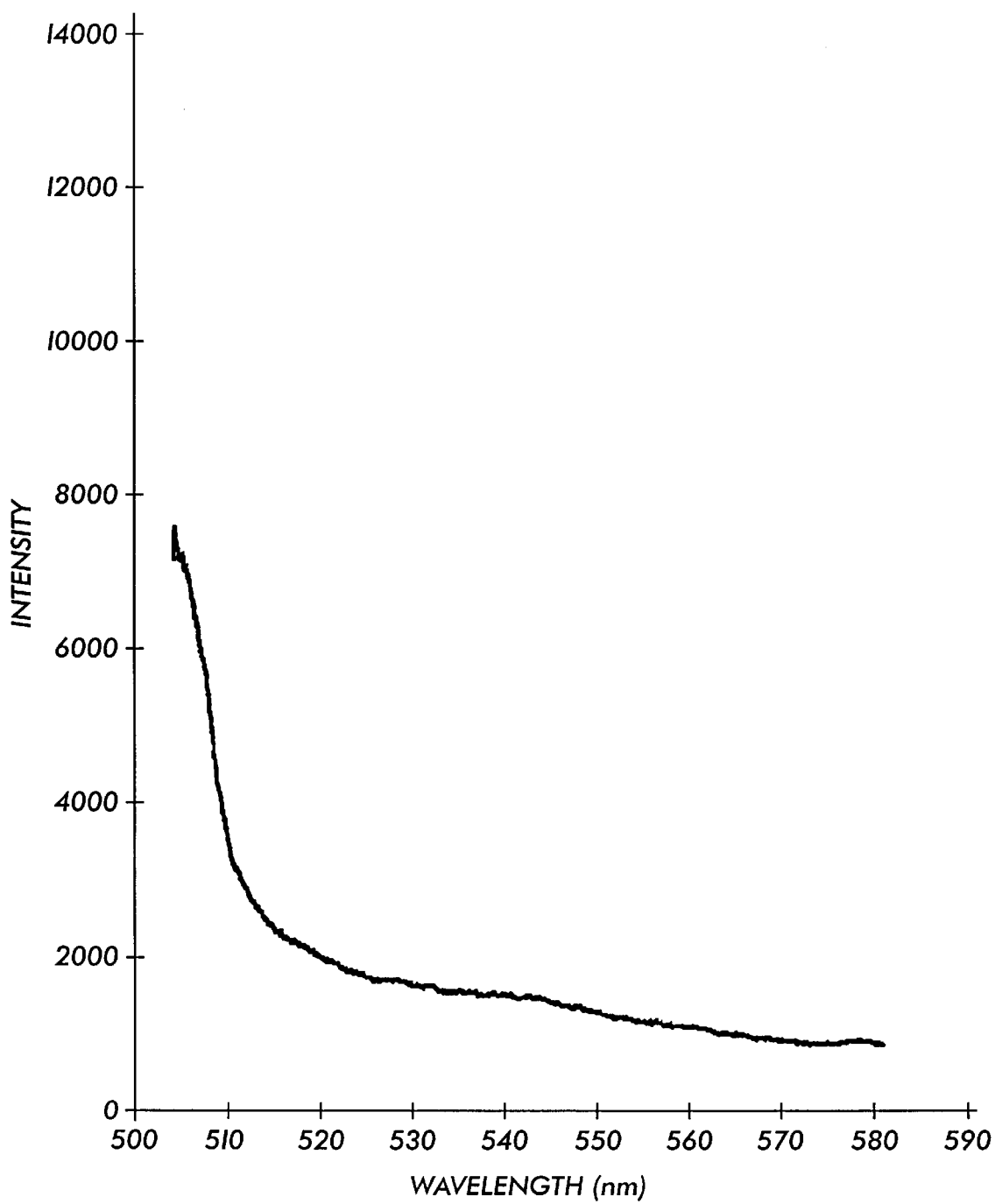
Figure 8B:
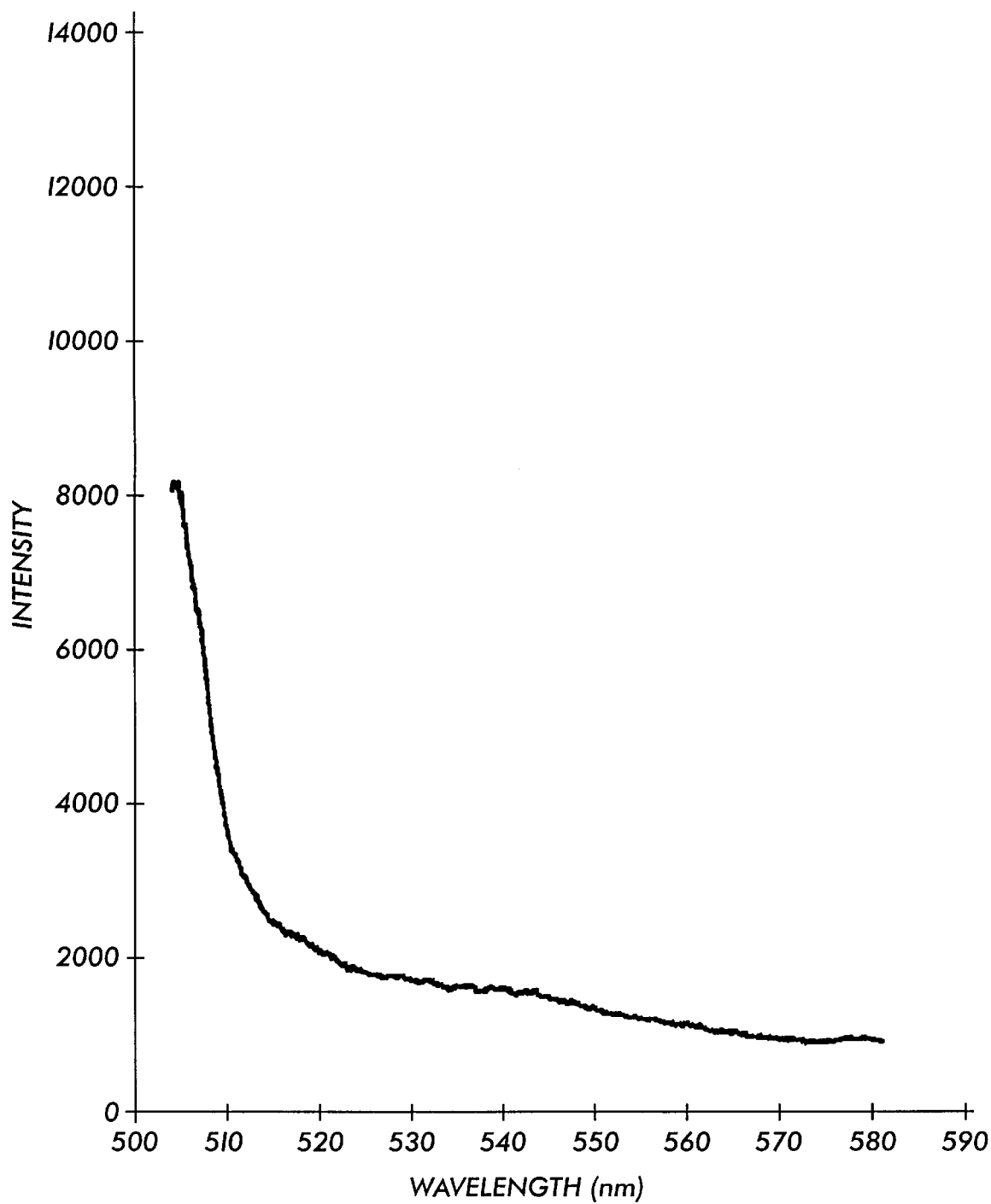

FIGS. 8A and 8B show the resulting fluorescence spectra. There was no evidence of hybridization complexes.

While the invention has been described in detail and with reference to specific examples thereof, it will be apparent to one skilled in the art that various changes and modifications can be made therein without departing from the spirit and scope thereof.

---

What is claimed is:

1. A method for detecting at least one single stranded or double stranded nucleotide sequence in a liquid medium, said method comprising:
providing said liquid medium comprising said at least one nucleotide sequence;
adding to said liquid medium at least one antisense probe to form at least one hybridization complex with said at least one nucleotide sequence, wherein said at least one probe comprises at least one marker; and
detecting said at least one nucleotide sequence by detecting at least one signal that is inversely proportional to an amount of said at least one hybridization complex in said liquid medium and proportional to an amount of said at least one probe unhybridized in said liquid medium,
wherein said method is conducted without separating unhybridized probes from said at least one hybridization complex prior to said signal detecting, and without providing a signal quenching agent on said at least one probe or on said at least one nucleotide sequence.

2. The method for detecting at least one nucleotide sequence according to claim 1, wherein said at least one probe has an uncharged backbone.

3. The method for detecting at least one nucleotide sequence according to claim 2, wherein said at least one probe comprises a PNA sequence.

4. The method for detecting at least one nucleotide sequence according to claim 1, wherein said at least one marker includes a fluorescent dye and said at least one signal is at least one fluorescent emission generated by irradiating said at least one marker with a light source.

5. The method for detecting at least one nucleotide sequence according to claim 4, wherein said light source is an argon ion laser which irradiates said at least one marker with light having a wavelength of about 200 to about 1000 nm.

6. The method for detecting at least one nucleotide sequence according to claim 5, wherein said at least one fluorescent emission is detected in a range of 200 to 1000 nm.

7. The method for detecting at least one nucleotide sequence according to claim 6, wherein said at least one signal is at least one fluorescent emission intensity generated by irradiating said at least one hybridization complex with a laser.

8. The method for detecting at least one nucleotide sequence according to claim 7, wherein a laser induced fluorescent intensity maximum of said liquid medium is compared with a laser induced fluorescent intensity maximum of a standard sample to detect whether said at least one nucleotide sequence is present in said liquid medium.

9. The method for detecting at least one nucleotide sequence according to claim 8, wherein a fluorescent intensity quenching effect correlated with probe to nucleotide sequence hybridization efficiency is analyzed to detect said at least one nucleotide sequence.

10. The method for detecting at least one nucleotide sequence according to claim 9, wherein a first said at least one probe is complementary to a first segment of a first nucleotide sequence, a second said at least one probe is complementary to a second segment of a second nucleotide sequence, and said first and second segments differ from each other.

11. The method for detecting at least one nucleotide sequence according to claim 10, wherein said first and second probes are completely complementary to said first and second segments, respectively.

12. The method for detecting at least one nucleotide sequence according to claim 11, wherein said first nucleotide sequence is complementary to said second nucleotide sequence.

13. The method for detecting at least one nucleotide sequence according to claim 12, wherein said first nucleotide sequence and said second nucleotide sequence are within opposing strands of double stranded DNA.

14. The method for detecting at least one nucleotide sequence according to claim 11, wherein said first nucleotide sequence and said second nucleotide sequence are in different genes.

15. The method for detecting at least one nucleotide sequence according to claim 14, wherein said first probe has a first marker which has a first fluorescent emission intensity at a first wavelength, said second probe has a second marker which has a second fluorescent emission intensity at a second wavelength, said first and second wavelengths are different, said first nucleotide sequence is detected by monitoring fluorescent emission intensity at said first wavelength and said second nucleotide sequence is detected by monitoring fluorescent emission intensity at said second wavelength.

16. The method for detecting at least one nucleotide sequence according to claim 11, wherein said first probe has a first marker which has a first fluorescent emission intensity at a first wavelength, said second probe has a second marker which has a second fluorescent emission intensity at a second wavelength, said first and second wavelengths are different, said first nucleotide sequence is detected by monitoring fluorescent emission intensity at said first wavelength and said second nucleotide sequence is detected by monitoring fluorescent emission intensity at said second wavelength.

17. The method for detecting at least one nucleotide sequence according to claim 16, wherein said first nucleotide sequence is a positive control expected to be present in said liquid medium being analyzed, and said second nucleotide sequence is detected by comparing said first intensity and said second intensity.

18. The method for detecting at least one nucleotide sequence according to claim 17, wherein the second nucleotide sequence is found only in a mutant genomic DNA and the first nucleotide sequence is found in said mutant genomic DNA and in a corresponding wild type genomic DNA.

19. The method for detecting at least one nucleotide sequence according to claim 18, wherein the first and second markers are selected from the group consisting of fluorescein and rhodamine.

20. The method for detecting at least one nucleotide sequence according to claim 17, wherein a third probe having a third marker which has a third fluorescent emission intensity at a third wavelength differing from the first and second wavelengths is added to said liquid medium as a negative control which is not expected to hybridize with any nucleotide sequence, and said second nucleotide sequence is detected by comparing the first, second and third intensities.

21. The method for detecting at least one nucleotide sequence according to claim 9, wherein prior to subjecting said liquid medium to hybridizing conditions, said liquid medium is divided into a plurality of equal portions with a different probe in each portion, and the laser induced fluorescent intensities of said portions are compared to determine which probe is most complementary to said at least one nucleotide sequence.

22. The method for detecting at least one nucleotide sequence according to claim 9, wherein at least two different types of probes differing by at least one base are fixed to different internal surfaces of a container in which said liquid medium is added, and after subjecting the liquid medium to hybridization conditions and fluorescence inducing radiation, fluorescent intensities emanating from the different surfaces of the container are compared to determine whether the sample contains a nucleotide sequence perfectly complementary to either or both types of said probes fixed to the surface.

23. The method for detecting at least one nucleotide sequence according to claim 1, further comprising determining a hybridization efficiency of said at least one probe with respect to said at least one nucleotide sequence.

24. The method for detecting at least one nucleotide sequence according to claim 1, wherein said at least one nucleotide sequence is mRNA, and antisense drug accessible segments of said mRNA are identified by comparing the fluorescent intensities of a plurality of different probes for a plurality of different segments of said mRNA.

25. The method for detecting at least one nucleotide sequence according to claim 1, further comprising comparing the fluorescent intensities of a plurality of different probes for a single segment of said at least one nucleotide sequence to determine a number of base mismatches between each of said probes and said segment.

26. The method for detecting at least one nucleotide sequence according to claim 1, further comprising detecting locations of a plurality of nucleotide sequences within a genome to map said genome.

27. The method for detecting at least one nucleotide sequence according to claim 1, wherein said at least one marker is one fluorophore, and said one fluorophore is the only fluorophore on said at least one probe.

28. The method for detecting at least one nucleotide sequence according to claim 1, wherein said method is conducted without using enzymes to digest said probe.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 150 bases
        ( B ) TYPE: nucleotide
        ( C ) STRANDEDNESS: double- stranded
        ( D ) TOPOLOGY: linear ( i i ) MOLECULE TYPE: genomic DNA ( x i ) SEQUENCE DESCRIPTION: SEQ ID NO:1:

```
AACACCAGCT   CCTCTCCCCA   GCCAAAGAAG   AAACCACTGG   ATGGAGAATA   TTTCACCCTT       60

CAGATCCGTG   GGCGTGAGCG   CTTCGAGATG   TTCCGAGAGC   TGAATGAGGC   CTTGGAACTC      120

AAGGATGCCC   AGGCTGGGAA   GGAGCCAGGG                                            150
```

( 2 ) INFORMATION FOR SEQ ID NO:2:

( i ) SEQUENCE CHARACTERISTICS:
        ( A ) LENGTH: 150 bases
        ( B ) TYPE: nucleotide
        ( C ) STRANDEDNESS: double- stranded (D) TOPOLOGY: linear (ii) MOLECULE TYPE: genomic DNA (xi) SEQUENCE DESCRIPTION: SEQ ID NO:2:

```
AACACCAGCT CCTCTCCCCA GCCAAAGAAG AAACCACTGG ATGGAGAATA TTTCACCCTT      60
CAGATCCGTG GGCGTGAGCG CTTCGAGATG TTCCGAGAGC AGAATGAGGC CTTGGAACTC     120
AAGGATGCCC AGGCTGGGAA GGAGCCAGGG                                      150
```

(2) INFORMATION FOR SEQ ID NO:3:

(i) SEQUENCE CHARACTERISTICS:
        (A) LENGTH: 150 bases
        (B) TYPE: nucleotide
        (C) STRANDEDNESS: double-stranded
        (D) TOPOLOGY: linear (ii) MOLECULE TYPE: genomic DNA (xi) SEQUENCE DESCRIPTION: SEQ ID NO:3:

```
AACACCAGCT CCTCTCCCCA GCCAAAGAAG AAACCACTGG ATGGAGAATA TTTCACCCTT      60
CAGATCCGTG GGCGTGAGCG CTTCGAGATG TTCCGAGAGC GGAATGAGGC CTTGGAACTC     120
AAGGATGCCC AGGCTGGGAA GGAGCCAGGG                                      150
```

(2) INFORMATION FOR SEQ ID NO:4:

(i) SEQUENCE CHARACTERISTICS:
        (A) LENGTH: 150 bases
        (B) TYPE: nucleotide
        (C) STRANDEDNESS: double-stranded
        (D) TOPOLOGY: linear (ii) MOLECULE TYPE: genomic DNA (xi) SEQUENCE DESCRIPTION: SEQ ID NO:4:

```
AACACCAGCT CCTCTCCCCA GCCAAAGAAG AAACCACTGG ATGGAGAATA TTTCACCCTT      60
CAGATCCGTG GGCGTGAGCG CTTCGAGATG TTCCGAGAGA AGAATGAGGC CTTGGAACTC     120
AAGGATGCCC AGGCTGGGAA GGAGCCAGGG                                      150
```

(2) INFORMATION FOR SEQ ID NO:5:

(i) SEQUENCE CHARACTERISTICS:
        (A) LENGTH: 150 bases
        (B) TYPE: nucleotide
        (C) STRANDEDNESS: double-stranded
        (D) TOPOLOGY: linear (ii) MOLECULE TYPE: genomic DNA (xi) SEQUENCE DESCRIPTION: SEQ ID NO:5:

```
AACACCAGCT CCTCTCCCCA GCCAAAGAAG AAACCACTGG ATGGAGAATA TTTCACCCTT      60
CAGATCCGTG GGCGTGAGCG CTTCGAGATG TTCCGAGAGT ACAATGAGGC CTTGGAACTC     120
AAGGATGCCC AGGCTGGGAA GGAGCCAGGG                                      150
```

(2) INFORMATION FOR SEQ ID NO:6:

(i) SEQUENCE CHARACTERISTICS:
        (A) LENGTH: 633 bases
        (B) TYPE: nucleotide
        (C) STRANDEDNESS: double-stranded
        (D) TOPOLOGY: linear (ii) MOLECULE TYPE: genomic DNA (xi) SEQUENCE DESCRIPTION: SEQ ID NO:6:

| | | | | | | |
|---|---|---|---|---|---|---|
| CCGGCGGCCC | CTGCACCAGC | CCCCTCCTGG | CCCTGTCAT | CTTCTGTCCC | TTCCCAGAAA | 60 |
| ACCTACCAGG | GCAGCTACGG | TTTCCGTCTG | GGCTTCTTGC | ATTCTGGGAC | AGCCAAGTCT | 120 |
| GTGACTTGCA | CGTACTCCCC | TGCCCTCAAC | AAGATGTTTT | GCCAACTGGC | CAAGACCTGC | 180 |
| CCTGTGCAGC | TGTGGGTTGA | TTCCACACCC | CCGCCCGGCA | CCCGCGTCCG | CGCCATGGCC | 240 |
| ATCTACAAGC | AGTCACAGCA | CATGACGGAG | GTTGTGAGGC | GCTGCCCCA | CCATGAGCGC | 300 |
| TGCTCAGATA | GCGATGGTCT | GGCCCCTCCT | CAGCATCTTA | TCCGAGTGGA | AGGAAATTTG | 360 |
| CGTGTGGAGT | ATTTGGATGA | CAGAAACACT | TTTCGACATA | GTGTGGTGGT | GCCCTATGAG | 420 |
| CCGCCTGAGG | TTGGCTCTGA | CTGTACCACC | ATCCACTACA | ACTACATGTG | TAACAGTTCC | 480 |
| TGCATGGGCG | GCATGAACCG | GAGGCCCATC | CTCACCATCA | TCACACTGGA | AGACTCCAGT | 540 |
| GGTAATCTAC | TGGGACGGAA | CAGCTTTGAG | GTGCGTGTTT | GTGCCTGTCC | TGGGAGAGAC | 600 |
| CGGCGCACAG | AGGAAGAGAA | TCTCCGCAAG | AAA | | | 633 |